United States Patent [19]

Kinoshita et al.

[11] Patent Number: 4,541,902
[45] Date of Patent: Sep. 17, 1985

[54] ANALYTICAL METHOD FOR DETERMINING FORMALDEHYDE IN ELECTROLESS COPPER PLATING BATH

[75] Inventors: Akemi Kinoshita, Higashiosaka; Ken Araki, Ibaragi; Hidemi Nawafune, Takatsuki; Shozo Mizumoto, Takarazuka, all of Japan

[73] Assignee: C. Uyemura & Co., Ltd., Osaka, Japan

[21] Appl. No.: 668,956

[22] Filed: Nov. 7, 1984

[30] Foreign Application Priority Data

Nov. 11, 1983 [JP] Japan ................. 58-212066

[51] Int. Cl.$^4$ ............................. G01N 27/46
[52] U.S. Cl. ................... 204/1 T; 204/405; 422/75; 422/76; 427/305
[58] Field of Search ............. 204/1 M, 405; 422/75, 422/76

[56] References Cited

U.S. PATENT DOCUMENTS

| 3,551,109 | 12/1970 | Dahms | 204/405 |
| 3,655,526 | 4/1972 | Christian | 204/1 M |
| 3,697,224 | 10/1972 | Means | 422/75 |

FOREIGN PATENT DOCUMENTS 1577565 10/1980 United Kingdom ........... 204/405

Primary Examiner—T. Tung
Attorney, Agent, or Firm—Birch, Stewart, Kolasch & Birch

[57] ABSTRACT

An analytical method for determining by potentiometric titration formaldehyde in an electroless copper plating bath, which comprises using a hydroxylamine salt such as hydroxylamine hydrochloride as the titrant and using a silver electrode as the indicator electrode. This method can determine free formaldehyde in low concentration which takes part in the plating reaction.

10 Claims, 8 Drawing Figures

FIG.4
(1)
(2)
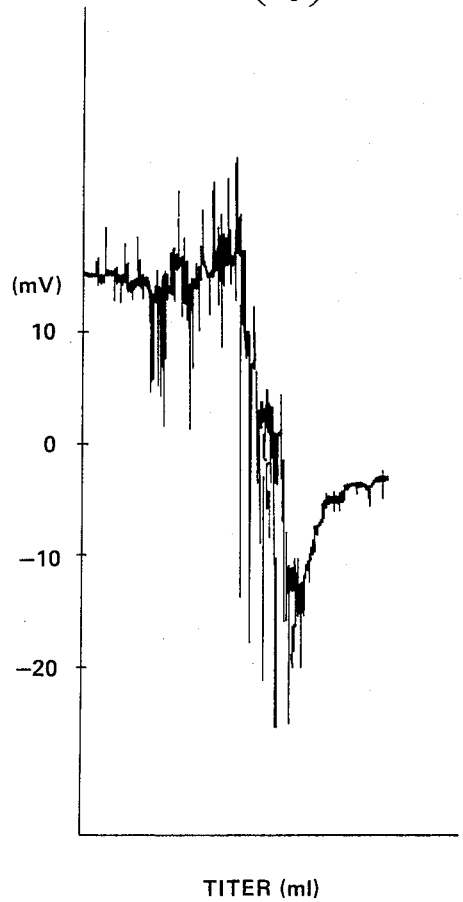
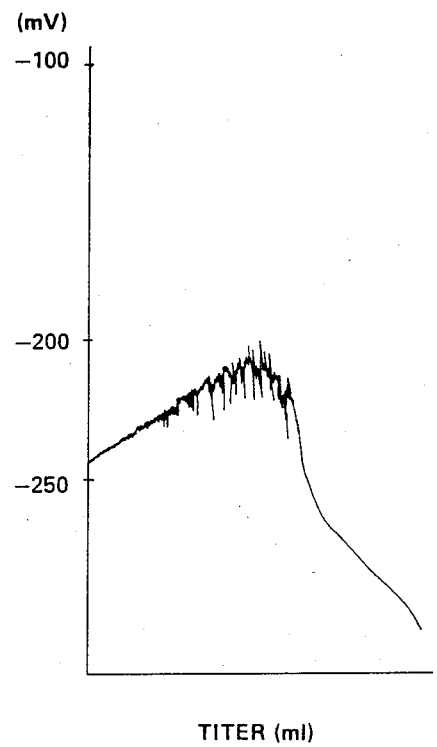

FIG.4
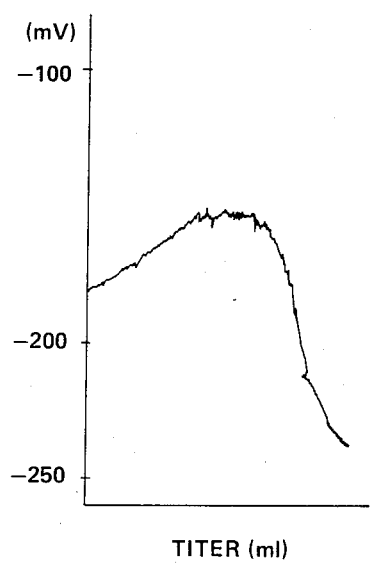
(3)
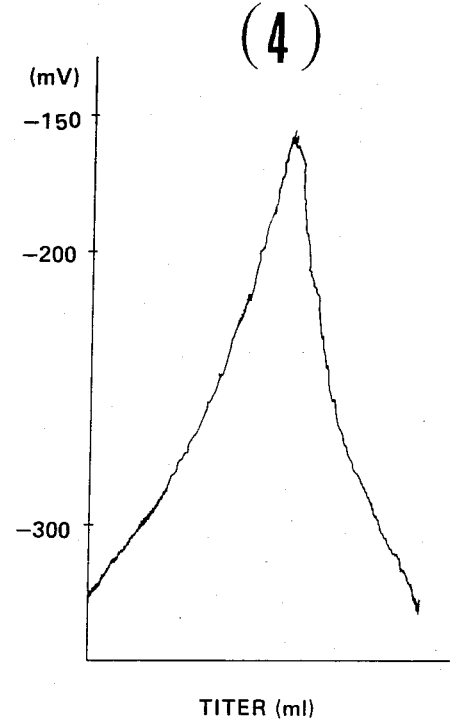
(4)

FIG.4
(5)
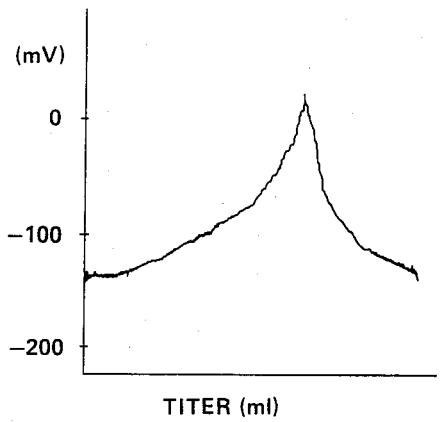
(6)
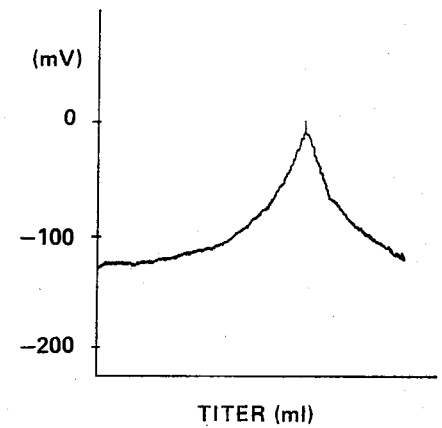
(7)
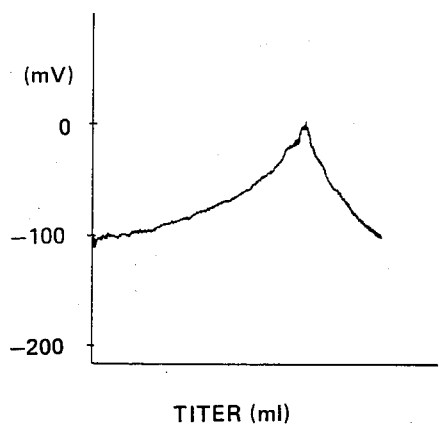
(8)
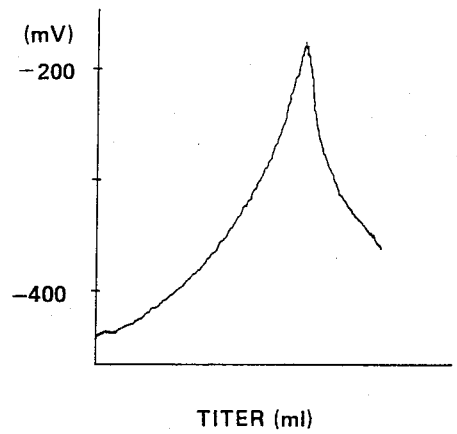

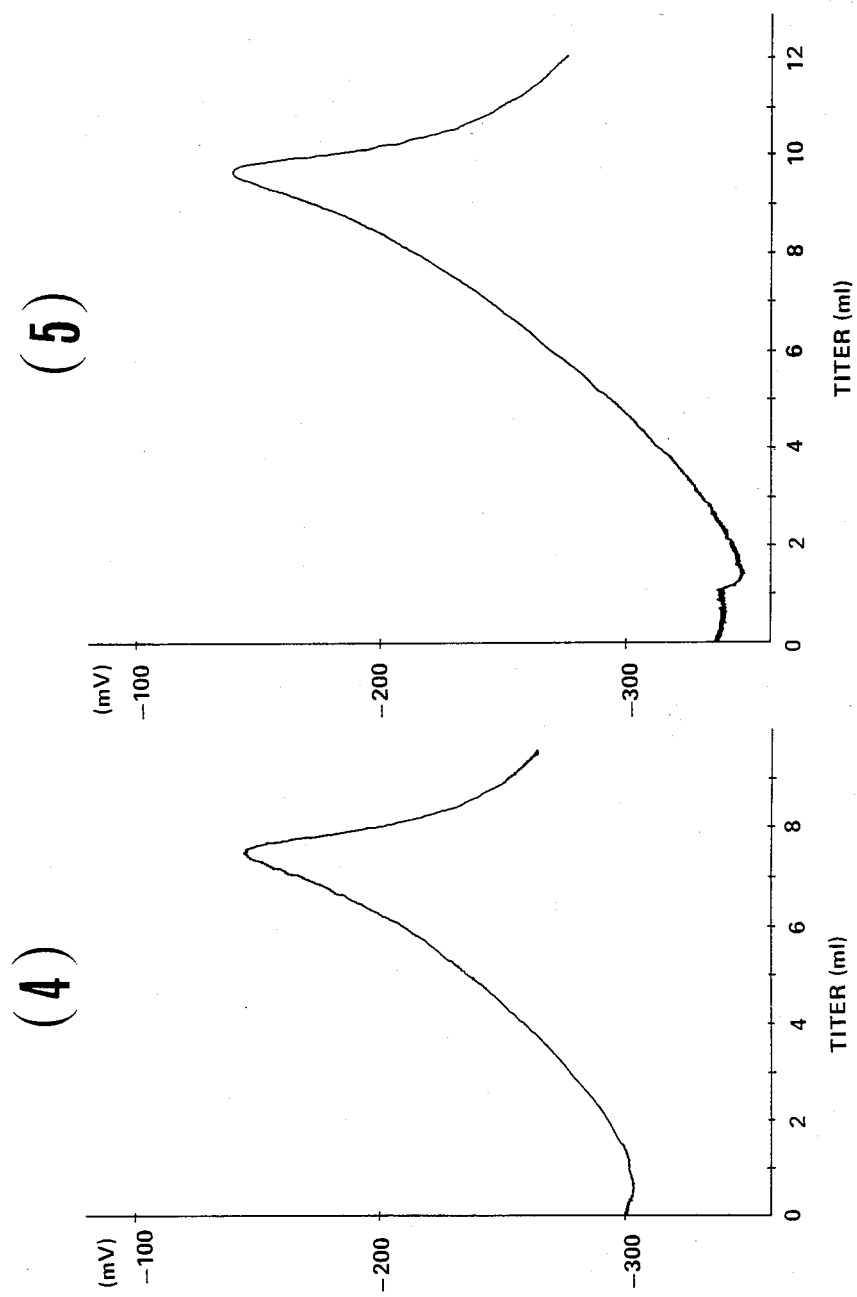

FIG.5
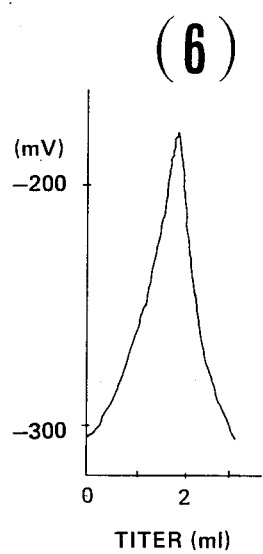
(6)
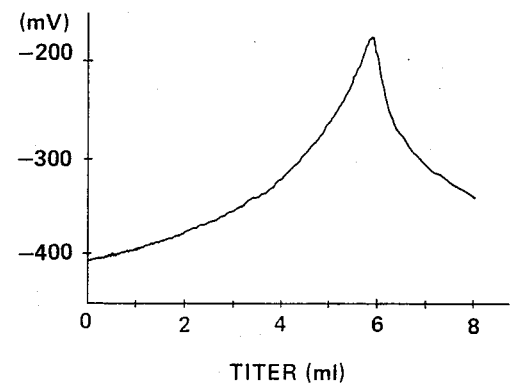
(7)
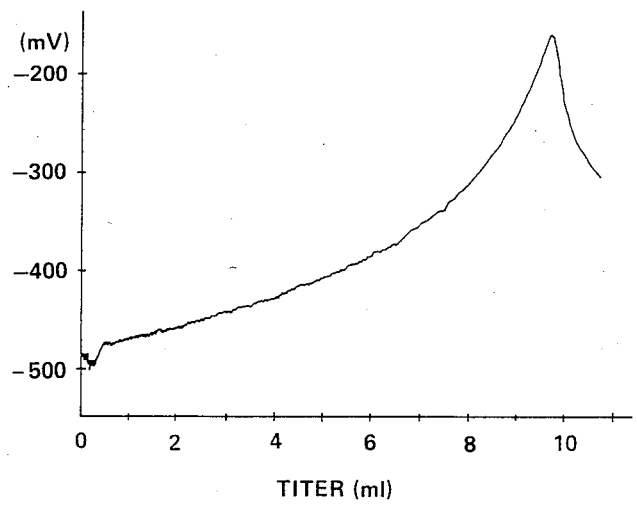
(8)

FIG.8
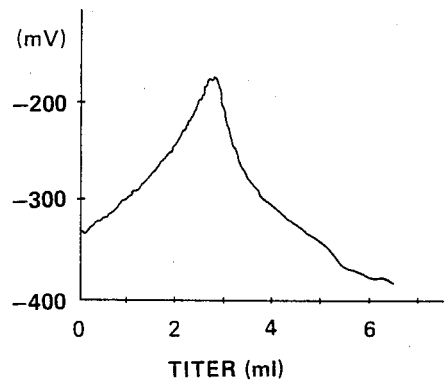
(1)
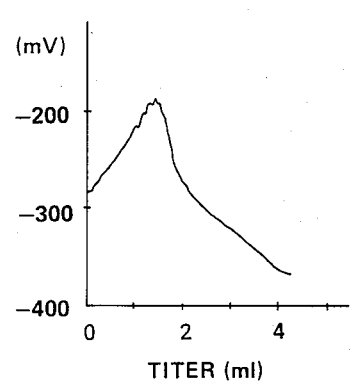
(2)
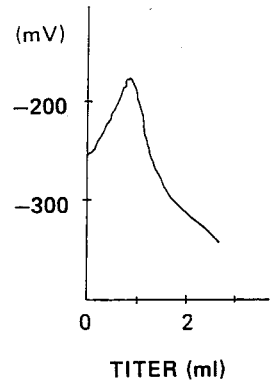
(3)
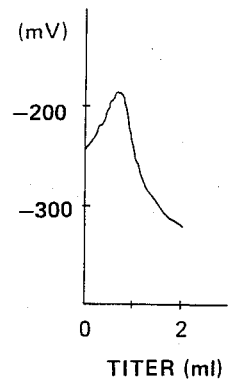
(4)

ANALYTICAL METHOD FOR DETERMINING FORMALDEHYDE IN ELECTROLESS COPPER PLATING BATH

BACKGROUND OF THE INVENTION

The present invention relates to an analytical method for determining formaldehyde in an electroless copper plating bath.

An electroless copper plating bath usually contains cupric ions, a complexing agent that forms a complex compound with cupric ions, and formaldehyde as a reducing agent. It has a comparatively high pH value. As the electroless copper plating proceeds, the concentrations of cupric ions and formaldehyde decrease and the pH goes down. The change in concentrations lowers the deposition rate of electroless copper plating and fluctuates the physical properties of the electroless copper deposit. Thus it is necessary to measure the concentrations of cupric ions and formaldehyde in the electroless copper plating bath and the pH of the bath continuously or intermittently, and to keep a prescribed level of concentrations by replenishing them and to keep the pH at a prescribed value.

Heretofore, there have been proposed various methods for analyzing the components of the electroless copper plating bath. For example, the quantity of formaldehyde in the plating bath is determined by using a sulfite (sodium sulfite). This method utilizes the addition reaction of formaldehyde with sodium sulfite. According to this method, the plating solution is neutralized to a certain level of pH with a prescribed amount of acid aqueous solution of predetermined concentration, and then sodium sulfite is added to the neutralized plating solution. Formaldehyde reacts with sodium sulfite to give sodium hydroxide as shown in the following equation.

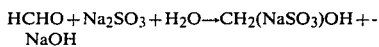

$$HCHO + Na_2SO_3 + H_2O \rightarrow CH_2(NaSO_3)OH + NaOH$$

The sodium hydroxide thus formed changes the pH. Therefore, the quantity of formaldehyde can be determined by measuring the pH change with a pH meter, or by determining the quantity of sodium hydroxide with acidimetry to restore the original pH of the neutralized plating solution.

This method, however, has a disadvantage of causing errors that make analytical values smaller than correct ones. This is inevitable because the plating solution is adjusted to pH 9–10 before the addition of sodium sulfite in order to avoid the effect of other components in the plating bath. At this pH level, the above-mentioned reaction is slow and incomplete, particularly where the concentration of formaldehyde is low. In practice, the analytical values obtained by this method are corrected by an empirical factor. Moreover, this method has another disadvantage attributable to the use of a pH meter. The glass electrode of a pH meter tends to cause errors when deteriorated by the strong basicity (pH 13–14) resulting from sodium sulfite added.

Recently, a new type of electroless copper plating bath has appeared. It is incorporated with a compound such as glycine which forms an addition product with formaldehyde, so that the activity of formaldehyde is controlled. In using this plating bath, it is necessary to control the concentration of free formaldehyde which remains unreacted with the compound to form an addition product. Free formaldehyde greatly affects the deposition rate of the electroless copper plating and the physical properties of the copper deposits. The sodium sulfite method has a disadvantage that it determines total formaldehyde, but does not selectively determine free formaldehyde.

In addition to the above-mentioned method, there is known a titrimetric method that employs an iodine solution for the determination of formaldehyde in the plating bath. This method is limited in application and impracticable, because iodine can react with a complexing agent or other components in the plating bath.

In consideration of the foregoing, the present inventors carried out extensive studies on the analytical method for determining formaldehyde in the electroless copper plating bath, with great emphasis on the method that gives accurate results even in the case where the concentration of formaldehyde is low and on the method capable of determining free formaldehyde directly in the case where the plating solution is incorporated with a compound that forms an addition product with formaldehyde. As the result, it was found that this object can be achieved by potentiometric titration in which a hydroxylamine salt such as hydroxylamine hydrochloride is used as the titrant and a silver electrode as the indicator electrode. The present invention was completed based on this finding.

SUMMARY OF THE INVENTION

Accordingly, it is an object of this invention to provide an analytical method for determining by potentiometric titration formaldehyde in an electroless copper plating bath which comprises using a hydroxylamine salt such as hydroxylamine hydrochloride as the titrant and a silver electrode as the indicator electrode.

According to the present invention, the silver electrode indicates clearly the end point of the potentiometric titration of the electroless copper plating solution sample containing copper ions and a complexing agent, resulting in the accurate determination of formaldehyde in the bath, even when the concentration of formaldehyde is as low as 0.006 mol/liter and the concentrations of copper and complexing agent fluctuate. Moreover, when a compound that forms an addition product with formaldehyde is added to the electroless plating bath, it is possible to determine selectively and directly free formaldehyde which remains unreacted with the compound to form an addition product and exists in HCHO as it is. Since the free formaldehyde directly takes part in the plating reaction, the analytical method of formaldehyde according to the present invention is very effective for an electroless plating bath containing a compound that forms an addition product with formaldehyde.

The above and other objects, features and advantages of the invention will become more apparent from the following description in conjunction with the drawings.

BRIEF DESCRIPTION OF THE DRAWINGS

FIG. 4 (1) to (8) are graphs showing the results of potentiometric titration performed with different electrodes for the determination of formaldehyde in the electroless copper plating bath. (1) for Pt-Au electrodes, (2) for Pt-Ag/AgCl electrodes, (3) for Au-Ag/AgCl electrodes, (4) for Ag-Ag/AgCl electrodes, (5) Ag-Pt electrodes, (6) for Ag-Au electrodes, (7) for Ag-Ag electrodes, and (8) Ag-calomel electrodes.

FIG. 8 (1) to (4) are graphs showing the results of determination of formaldehyde in electroless copper plating baths each containing 0.04, 0.06, 0.08, and 0.10 mol/liter of glycine, performed by using Ag-Ag/AgCl electrodes.

DETAILED DESCRIPTION OF THE INVENTION

In the analytical method for determining formaldehyde in an electroless plating bath according to the present invention, a potentiometric titration method is employed in which formaldehyde in the electroless plating solution sample is titrated with a hydroxylamine salt and the end point of the titration is detected by using an indicator electrode consisting of a silver electrode and a reference electrode. As the hydroxylamine salt, hydroxylamine hydrochloride, hydroxylamine sulfate, hydroxylamine oxalate and the like are used. Among them, hydroxylamine hydrochloride is most preferred.

The reaction of formaldehyde with hydroxylamine hydrochloride is represented by the following equation.

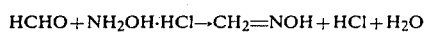

$$HCHO + NH_2OH \cdot HCl \rightarrow CH_2=NOH + HCl + H_2O$$

The hydroxylamine salt such as hydroxylamine hydrochloride used in this invention is not specifically limited in concentration. In general, it may be used in the form of aqueous solution of 0.01 to 0.1 mol/liter in concentration, depending on the sample quantity of electroless copper plating bath. The titration is carried out in an alkali pH range by adding an alkali such as an alkali metal hydroxide (including sodium hydroxide and potassium hydroxide), an alkali metal carbonate, an alkali metal becarbonate, an alkali earth metal hydroxide and the like to a sample solution. The hydroxylamine salt is dropped to this alkali sample solution.

According to this invention, the potentiometric titration is performed in the usual way, except that a silver electrode is used as the indicator electrode. The silver electrode indicates clearly the end point of titration as shown in the Examples given later. This permits the accurate determination of formaldehyde. Other indicator electrodes such as platinum electrode and gold electrode do not indicate the end point clearly and often cause considerable errors in the determination of formaldehyde.

Figure 1:
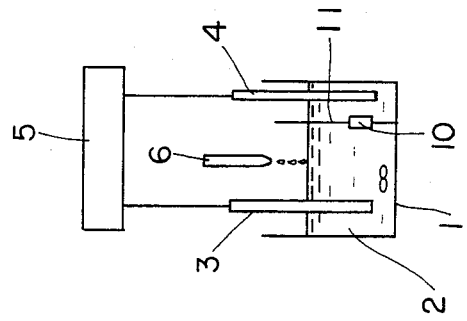
FIGS. 1 to 3 are diagrammatic illustrations of apparatus suitable for carrying out several embodiments of the present invention.
Figure 2:
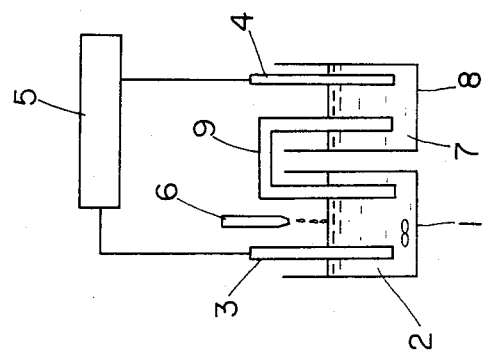
Figure 3:
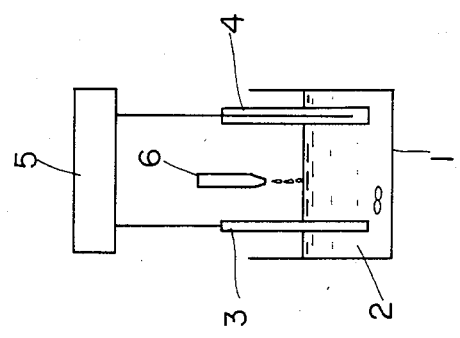

According to this invention, the reference electrode is selected from a silver chloride electrode, calomel electrode, platinum electrode, gold electrode, and silver electrode. A reference electrode such as silver chloride electrode and calomel electrode which contains an internal solution therein can be immersed directly in the plating solution as FIG. 1 shows. In FIG. 1, there are shown a plating solution container 1, a plating solution 2, an indicator electrode (silver electrode) 3, a reference electrode 4, a recording potentiometer 5, and a buret for dropping hydroxylamine hydrochloride 6. Where a platinum, gold, or silver electrode is used as the reference electrode, a provision may be made so that it does not come into direct contact with the sample solution (plating solution) in order to avoid the potential fluctuation caused by adsorption of the solution onto the electrode surface. This can be accomplished by providing a separate container 8 holding an electrode solution 7 as shown in FIG. 2. The reference electrode 4 is immersed in the electrode solution 7, and the electrode solution 7 and the plating solution 2 are connected by a salt bridge 9. Alternatively, the plating solution container 1 is divided into two compartments by a partition 11 having a porous part 10 such as ceramics and sintered glass as shown in FIG. 3. The electrode solution is selected from potassium chloride solution, which is usually used as an internal solution of an electrode, and any other solutions which transmit the potential in a stable manner. Examples of such solutions include an aqueous solution of EDTA or a mixture solution of EDTA and sodium hydroxide which may be a constituent of the electroless copper plating solution.

The analytical method of this invention can be applied to electroless copper plating baths of any type so long as they contains formaldehyde.

In general, the electroless copper plating bath contains copper ions which is supplied by copper sulfate or the like in an amount of 0.005 to 1 mol/liter, the agent for complexing cupric ions including ethylenediamine derivatives such as ethylenediaminetetraacetic acid, tetrahydroxy propyl ethylenediamine, N-hydroxy ethyl ethylenediaminetriacetic acid and the salts of these compounds; diethylenetriaminetriacetic acid, diethylenetriaminepentaacetic acid, nitrotriacetic acid, cyclohexylenediaminetetraacetic acid, citric acid, tartaric acid and the salts of these compounds in an amount of 0.01 to 3 mol/liter, formaldehyde in an amount of 0.01 to 0.5 mol/liter, and, as required, a stabilizer and other compounds.

According to the present invention, it accurately determines the concentration of formaldehyde even when the concentrations of copper and complexing agent fluctuate in the electroless copper plating bath. Moreover, it can determine formaldehyde in as low concentration as 0.01 mol/liter.

The analytical method of this invention is suitably applied to the determination of formaldehyde in an electroless copper plating bath containing a compound that forms an addition product with formaldehyde. The compound that forms an addition product with formaldehyde is a water-soluble organic compound having at least two polar groups, at least one of which is an amino group or imino group, and it is preferably one in which the main chain is a saturated or unsaturated linear hydrocarbon having 1 to 200 carbon atoms. Examples of the compound include aminocarboxylic acids such as glycine and alanine, aminosulfonic acids, aminophosphonic acids, polyamines such as ethylene diamine, aminoalkanols, aminoethers, aminoketones, iminocarboxylic acids, iminosulfonic acids, iminophosphonic acids, iminoalcohols, iminoethers, and iminoketones. The compound may be added in an amount of 0.004 to 1 mole/liter. According to the analytical method of this invention, it is possible to determine selectively and directly free formaldehyde which takes part in the plating reaction and remains unreacted without forming an addition product with the above-mentioned compound. Thus the analytical method of this invention permits one to control the concentration of free formaldehyde and to control the deposition rate and the physical properties of the deposit in a simple manner with certainty.

The analytical method of this invention can be applied to an automatic apparatus designed to determine the concentration of formaldehyde in the electroless copper plating bath continuously or intermittently. Such an apparatus may be connected to a computer-controlled apparatus that replenished formaldehyde when the concentration of formaldehyde decreases below the prescribed level.

The invention is now described in more detail with reference to the Examples and Comparative Examples that follow.

EXAMPLE 1

An electroless copper plating solution of the following composition was used as a sample.

| | |
|---|---|
| $CuSO_4.5H_2O$ | 0.04 mol/liter |
| EDTA.4Na | 0.08 mol/liter |
| HCHO | 0.04 or 0.06 mol/liter |
| NaOH | 0.10 mol/liter |

1 ml of this solution was diluted with 30 ml of deionized water and 10 ml of 1 N NaOH. Potentiometric titration was performed for this diluted solution with a 0.01 mol/liter aqueous solution of hydroxylamine hydrochloride, by using electrodes shown in Table 1. The results are shown in FIG. 4 (1) to (8).

TABLE 1

| Electrodes | | | |
|---|---|---|---|
| Indicator electrode | Reference electrode | Results | Remarks |
| Pt | Au* | FIG. 4 (1) | Comparative Example |
| Pt | Ag/AgCl* | FIG. 4 (2) | " |
| Au | Ag/AgCl* | FIG. 4 (3) | " |
| Ag | Ag/AgCl* | FIG. 4 (4) | Example |
| Ag | Pt** | FIG. 4 (5) | " |
| Ag | Au** | FIG. 4 (6) | " |
| Ag | Ag** | FIG. 4 (7) | " |
| Ag | Calomel* | FIG. 4 (8) | " |

*The electrode was immersed directly in the plating solution.
**A salt bridge was used.

It is to be noted from FIG. 4 that the end point of titration is detected clearly and certainly by the distinct peak that appears when the indicator electrode is Ag and the reference electrode is Ag/AgCl, Pt, Au, Ag, or calomel.

EXAMPLE 2

Electroless copper plating solutions of the following compositions were used as samples.

| | |
|---|---|
| $CuSO_4.5H_2O$ | 0.04 mol/liter |
| EDTA.4Na | 0.08 mol/liter |
| HCHO | 0.02 to 0.10 mol/liter |
| NaOH | 0.10 mol/liter |

Samples of predetermined quantities were taken, and each sample was diluted with 30 ml of deionized water and 10 ml of 1 N NaOH. Potentiometric titration was performed for each diluted solution with an aqueous solution of hydroxylamine hydrochloride of varied concentration by using Ag-Ag/AgCl electrodes. The titration conditions are shown in Table 2 and the results are shown in FIG. 5.

TABLE 2

Figure 5:
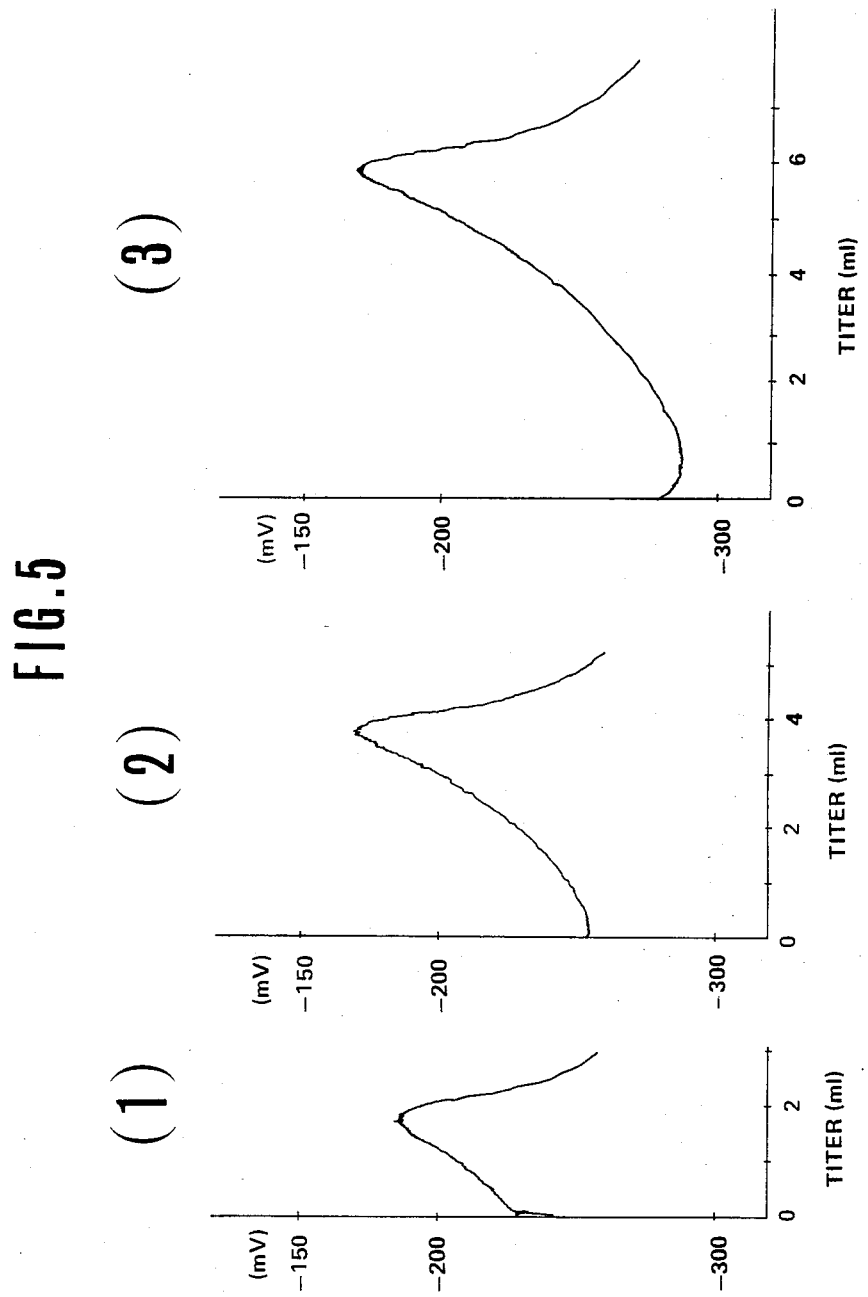
FIG. 5 (1) to (11) are also graphs showing the results of potentiometric titration performed with the Ag-Ag/AgCl electrodes for the determination of formaldehyde in the electroless copper plating bath. (1) to (5) show the results obtained when electroless copper plating baths each containing 0.02, 0.04, 0.06, 0.08, and 0.10 mol/liter of HCOH were analyzed by using a 0.01 mol/liter aqueous solution of hydroxylamine hydrochloride. (6) to (8) show the results obtained when electroless copper plating baths each containing 0.02, 0.06, and 0.10 mol/liter of HCOH were analyzed by using a 0.05 mol/liter aqueous solution of hydroxylamine hydrochloride. (9) to (11) show the results obtained when electroless copper plating baths each containing 0.02, 0.06, and 0.10 mol/liter of HCOH were analyzed by using a 0.10 mol/liter aqueous solution of hydroxylamine hydrochloride.
Figure 5:
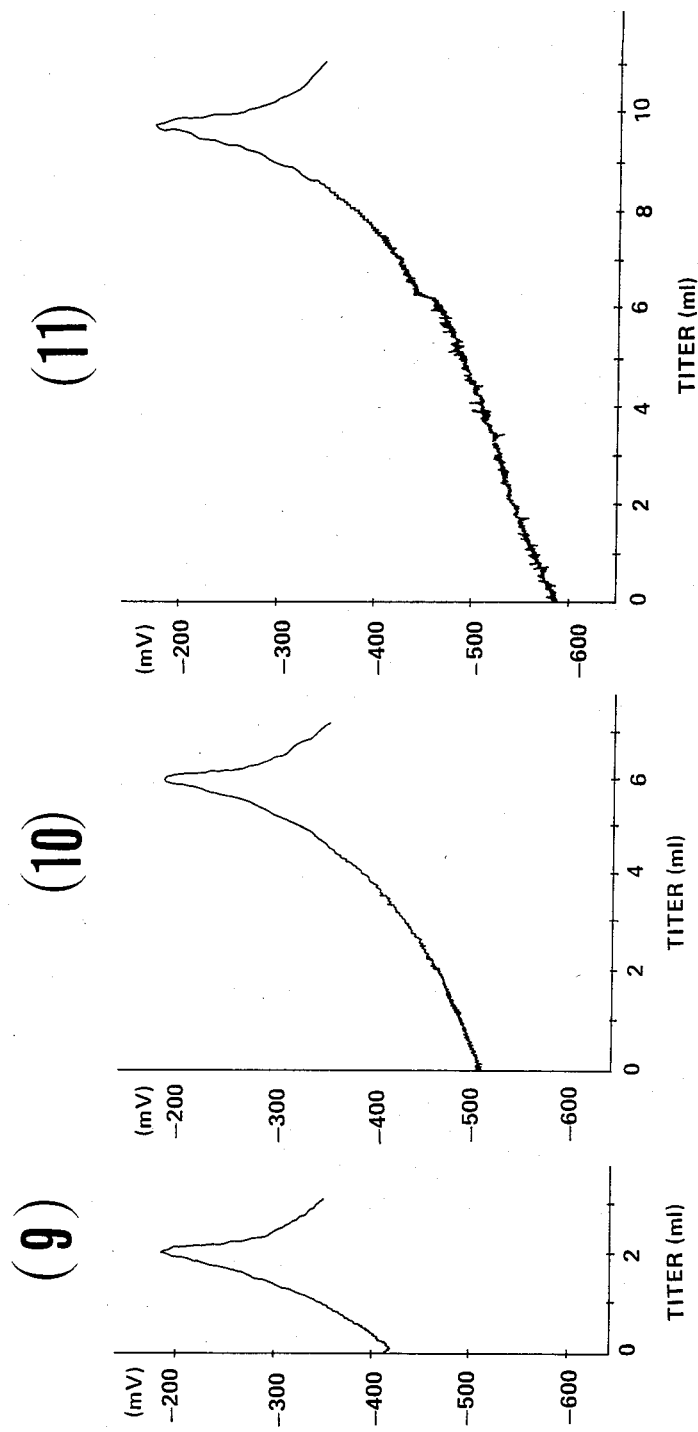

| Concentration of HCHO | Sample quantity of plating solution | Concentration of $NH_2OH.HCl$ used for titration | Results |
|---|---|---|---|
| 0.02 mol/L | 1 ml | 0.01 mol/L | FIG. 5 (1) |
| 0.04 mol/L | 1 ml | 0.01 mol/L | FIG. 5 (2) |
| 0.06 mol/L | 1 ml | 0.01 mol/L | FIG. 5 (3) |
| 0.08 mol/L | 1 ml | 0.01 mol/L | FIG. 5 (4) |
| 0.10 mol/L | 1 ml | 0.01 mol/L | FIG. 5 (5) |
| 0.02 mol/L | 5 ml | 0.05 mol/L | FIG. 5 (6) |
| 0.06 mol/L | 5 ml | 0.05 mol/L | FIG. 5 (7) |
| 0.10 mol/L | 5 ml | 0.05 mol/L | FIG. 5 (8) |
| 0.02 mol/L | 10 ml | 0.10 mol/L | FIG. 5 (9) |
| 0.06 mol/L | 10 ml | 0.10 mol/L | FIG. 5 (10) |
| 0.10 mol/L | 10 ml | 0.10 mol/L | FIG. 5 (11) |

The results in this example indicate that the potentiometric titration with hydroxylamine hydrochloride using a silver electrode as the indicator electrode can determine formaldehyde of low concentration in an electroless copper plating bath.

Figure 6:
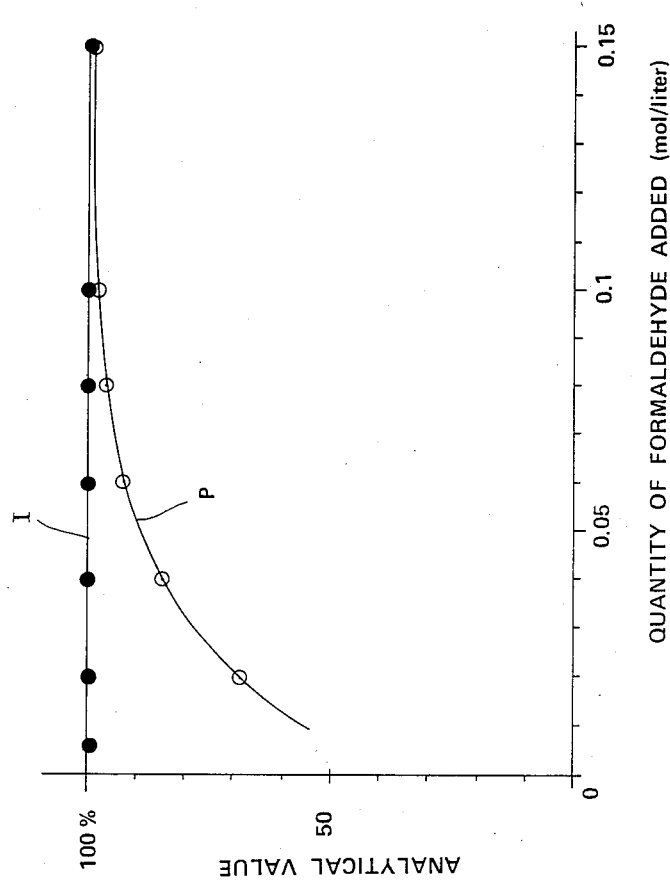
FIG. 6 is a graph showing the results of determination of formaldehyde of different concentrations in electroless copper plating baths, performed by the conventional sodium sulfite titration and the potentiometric titration (Ag-Ag/AgCl electrodes) of this invention which employs hydroxylamine hydrochloride.

In the meantime, FIG. 6 shows the results of determination of formaldehyde of different concentrations in electroless copper plating baths. The determination was performed according to the potentiometric titration (with Ag-Ag/AgCl electrodes) of this invention, and also according to the conventional titration with sodium sulfite. The analytical values plotted on the ordinate in FIG. 6 are those which are expressed by $A/B \times 100\%$, where A is the analytical value of formaldehyde and B is the quantity of formaldehyde added to the plating solution. In FIG. 6, "I" indicated the results of the invention method and "P" indicates the results of conventional sodium sulfite method.

Thre results in FIG. 6 indicate that the analytical method of this invention gives correct analytical values even when the concentration of formaldehyde is as low as 0.006 mol/liter, whereas the conventional analytical method gives greater errors as the concentration of formaldehyde decreases.

EXAMPLE 3

A 5-ml sample was taken from an electroless cooper plating solution of the following compsoition, and it was diluted with 30 ml of dieonized water and 10 ml of 1 N NaOH. Potentiometric titration was performed with a 0.05 mol/liter aqueous solution of hydroxylamine hydrochloride by using the Ag-Ag/AgCl electrodes.

| | |
|---|---|
| $CuSO_4.5H_2O$ | 0.02 to 0.06 mol/liter |
| EDTA.4Na | 0.0064 to 0.12 mol/liter |
| HCHO | 0.06 mol/liter |
| NaOH | 0.10 mol/liter |

Figure 7:
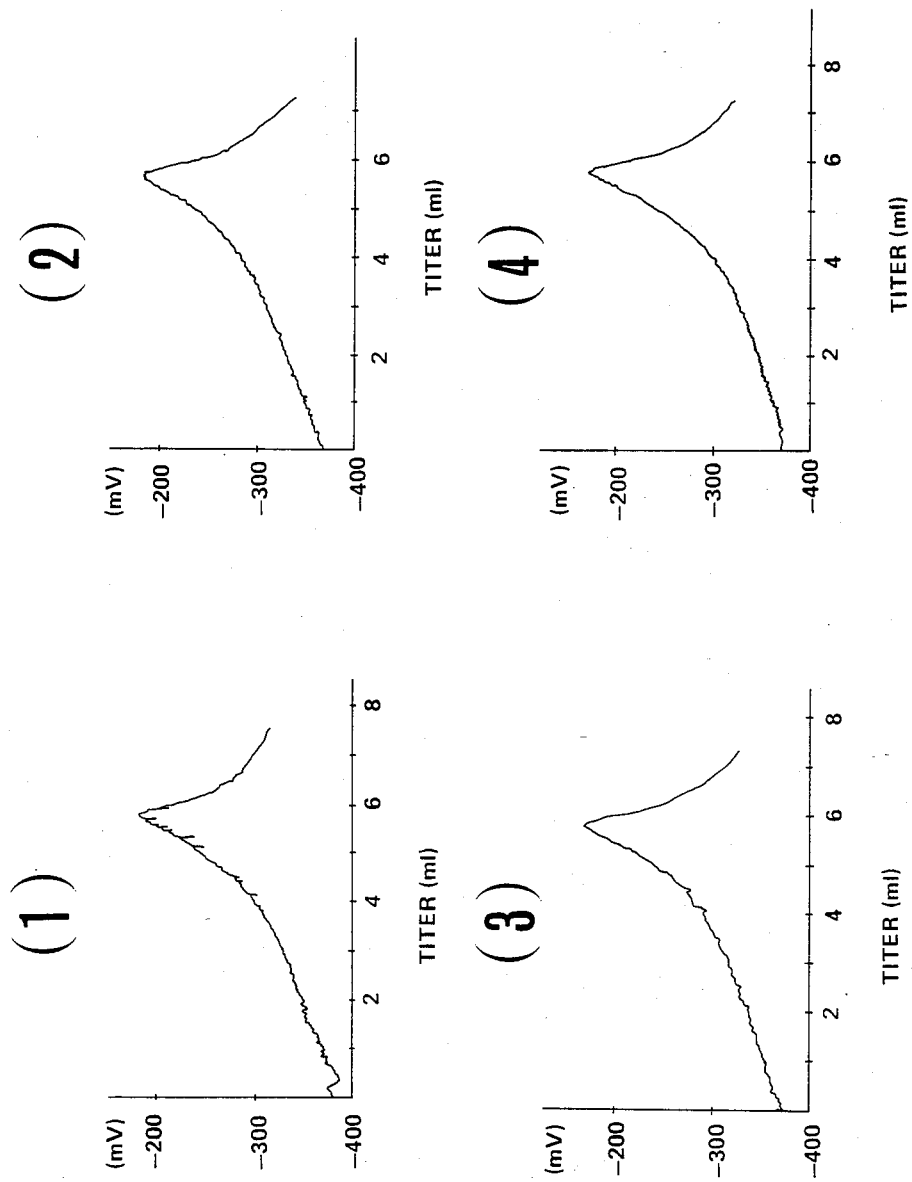
FIG. 7 (1) to (4) are graphs showing the results of determination performed by using Ag-Ag/AgCl electrodes. (1) and (2) show the results obtined in the case where the concentrations of copper are 0.02 and 0.06 mol/liter, respectively. (3) and (4) show the results obtained in the case where the concentrations of ED-TA-4Na are 0.064 and 0.12 mol/liter, respectively.

Table 3 shows the concentrations of copper and EDTA.4Na in the electroless copper plating solutions analyzed, and FIG. 7 shows the results of analyses.

TABLE 3

| Concentration of copper | Concentration of EDTA.4Na | Results |
|---|---|---|
| 0.02 mol/L | 0.08 mol/L | FIG. 7 (1) |
| 0.06 mol/L | 0.08 mol/L | FIG. 7 (2) |
| 0.04 mol/L | 0.064 mol/L | FIG. 7 (3) |
| 0.04 mol/L | 0.12 mol/L | FIG. 7 (4) |

The results in FIG. 7 indicate that the analytical method of this invention gives correct analytical values of formaldehyde even when the concentrations of copper and complexing agent (EDTA.4Na) in the plating bath fluctuate.

EXAMPLE 4

A 5-ml sample was taken from an electroless copper plating solution of the following composition, and it was diluted with 30 ml of deionized water and 10 ml of 1 N NaOH. Potentiometric titration was performed with a 0.05 mol/liter aqueous solution of hydroxylamine hydrochloride by using the Ag-Ag/AgCl electrodes.

| | |
|---|---|
| $CuSO_4.5H_2O$ | 0.04 mol/liter |
| EDTA.4Na | 0.08 mol/liter |
| HCHO | 0.06 mol/liter |
| Glycine | 0.04 to 0.10 mol/liter |
| NaOH | 0.10 mol/liter |

Table 4 shows the concentrations of glycine in the electroless copper plating solutions analyzed, and FIG. 8 shows the results of analyses.

TABLE 4

| Concentration of glycine | Results | Quantity of HCHO determined |
|---|---|---|
| 0.04 mol/L | FIG. 8 (1) | 0.029 mol/L |
| 0.06 mol/L | FIG. 8 (2) | 0.014 mol/L |
| 0.08 mol/L | FIG. 8 (3) | 0.009 mol/L |
| 0.10 mol/L | FIG. 8 (4) | 0.007 mol/L |

Table 4 and FIG. 8 indicate that the quantity of formaldehyde determined by the potentiometric titration with hydroxylamine hydrochloride decreases as the quantity of glycine increases. This suggests that the potentiometric titration determines the concentration of free formaldehyde.

In the meantime, there exists free formaldehyde in the electroless copper plating bath composed of copper sulfate, EDTA.4Na, formaldehyde, and glycine, because EDTA.4Na forms a complex compound with copper sulfate and glycine reacts with formaldehyde to give an addition product and the equilibrium between formaldehyde and the addition product forms free formaldehyde. And the free formaldehyde which does not form an addition product with glycine and remains unreacted as HCHO takes part in the reduction of copper.

Table 4 and FIG. 8 indicate that the analytical method of this invention is very practical in view of the fact that it is capable of determining the concentration of free formaldehyde which directly takes part in the plating reaction. One the other hand, the conventional titration with sodium sulfite invariably gives a value of about 0.06 mol/liter for the concentration of formaldehyde regardless of the quantity of glycine added. This suggests that the conventional method determines the quantity of total formaldehyde, some of which does not take part in the plating reaction.

What is claimed is:

1. An analytical method for determining by potentiometric titration formaldehyde in an electroless copper plating bath, which comprises using a hydroxylamine salt as the titrant and using a silver electrode as the indicator electrode.

2. An analytical method defined in claim 1, wherein the hydroxylamine salt is selected from the group consisting of hydrocylamine hydrochloride, hydroxylamine sulfate and hydroxylamine oxalane.

3. An analytical method defined in claim 2, wherein the hydroxylamine salt is hydroxylamihne hydrochloride.

4. An analytical method defined in claim 3, wherein the reference electrode for potentiometric titration is one which is selected from a silver chloride electrode, calomel electrode, platinum electrode, gold electrode, and silver electrode.

5. An alanlytical method defined in claim 3, wherein the electroless copper plating bath is one which contains a compound that forms an addition product with formaldehyde.

6. An analytical method defined in claim 2, wherein the reference electrode for potentiometric titration is one which is selected from a silver chloride electrode, calomel electrode, platinum electrode, gold electrode, and silver electrode.

7. An alanlytical method defined in claim 2, wherein the electroless copper plating bath is one which contains a compound that forms an addition product with formaldehyde.

8. An analytical method defined in claim 1, wherein the reference electrode for potentiometric titration is one which is selected from a silver chloride electrode, calomel electrode, platinum electrode, gold electrode, and silver electrode.

9. An analytical method defined in claim 8, wherein the electroless copper plating bath is one which contains a compound that forms an addition product with formaldehyde.

10. An analytical method defined in claim 1, wherein the electroless copper plating bath is one which contains a compound that forms an addition product with formaldehyde.

* * * * *